(12) United States Patent
Huster

(10) Patent No.: US 8,021,849 B2
(45) Date of Patent: Sep. 20, 2011

(54) METHODS AND KITS FOR THE DETERMINATION OF SIROLIMUS IN A SAMPLE

(75) Inventor: Michael S. Huster, Pleasanton, CA (US)

(73) Assignee: Siemens Healthcare Diagnostics Inc., Deerfield, IL (US)

( * ) Notice: Subject to any disclaimer, the term of this patent is extended or adjusted under 35 U.S.C. 154(b) by 741 days.

(21) Appl. No.: 10/983,137

(22) Filed: Nov. 5, 2004

(65) Prior Publication Data

US 2006/0099654 A1     May 11, 2006

(51) Int. Cl.
*G01N 33/53* (2006.01)

(52) U.S. Cl. ........ 435/7.1; 435/7.92; 435/345; 436/501; 436/518

(58) Field of Classification Search .................. 435/7.1, 435/7.92–7.95, 345; 436/501, 518, 524–528, 436/164, 174
See application file for complete search history.

(56) References Cited

U.S. PATENT DOCUMENTS

| | | |
|---|---|---|
| 4,153,447 A | 5/1979 | Boroschewski et al. |
| 4,683,136 A | 7/1987 | Milich et al. |
| 4,883,751 A | 11/1989 | Gitel et al. |
| 4,920,218 A | 4/1990 | Askin et al. |
| 5,023,264 A | 6/1991 | Caufield et al. |
| 5,068,323 A | 11/1991 | Wyvratt, Jr. et al. |
| 5,118,677 A | 6/1992 | Caufield |
| 5,118,678 A | 6/1992 | Kao et al. |
| 5,120,725 A | 6/1992 | Kao et al. |
| 5,120,726 A | 6/1992 | Failli et al. |
| 5,151,413 A | 9/1992 | Caufield et al. |
| 5,169,773 A | 12/1992 | Rosenthaler et al. |
| 5,194,447 A | 3/1993 | Kao |
| 5,233,025 A | 8/1993 | Miyazaki et al. |
| 5,258,389 A | 11/1993 | Goulet et al. |
| 5,260,300 A | 11/1993 | Hu |
| 5,283,190 A | 2/1994 | Traish et al. |
| 5,302,584 A | 4/1994 | Kao et al. |
| 5,354,845 A | 10/1994 | Soldin |
| 5,362,718 A | 11/1994 | Skotnicki et al. |
| 5,362,735 A | 11/1994 | Luengo |
| 5,373,014 A | 12/1994 | Failli et al. |
| 5,378,836 A | 1/1995 | Kao et al. |
| 5,385,909 A | 1/1995 | Nelson et al. |
| 5,391,730 A | 2/1995 | Skotnicki et al. |
| 5,411,967 A | 5/1995 | Kao et al. |
| 5,416,086 A | 5/1995 | Kao et al. |
| 5,432,183 A | 7/1995 | Schulte |
| 5,455,249 A | 10/1995 | Skotnicki et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,498,597 A | 3/1996 | Burakoff et al. |
| 5,503,987 A | 4/1996 | Wagner et al. |
| 5,504,091 A | 4/1996 | Molnar-Kimber et al. |
| 5,508,399 A | 4/1996 | Kao et al. |
| 5,525,523 A | 6/1996 | Soldin |
| 5,525,610 A | 6/1996 | Caufield et al. |
| 5,530,007 A | 6/1996 | Kao et al. |
| 5,559,120 A | 9/1996 | Kao et al. |
| 5,563,145 A | 10/1996 | Failli et al. |
| 5,583,139 A | 12/1996 | Or et al. |
| 5,648,361 A | 7/1997 | Holt et al. |
| 5,656,434 A | 8/1997 | Terano et al. |
| 5,661,156 A | 8/1997 | Holt et al. |
| 5,665,772 A | 9/1997 | Cottens et al. |
| 5,672,605 A | 9/1997 | Or et al. |
| 5,677,295 A | 10/1997 | Failli et al. |
| 5,728,710 A | 3/1998 | Luengo |
| 5,780,307 A | 7/1998 | Soldin |
| 5,912,253 A | 6/1999 | Cottens et al. |
| 5,922,730 A | 7/1999 | Hu et al. |
| 5,952,320 A | 9/1999 | Davidsen et al. |
| 5,985,890 A | 11/1999 | Cottens et al. |
| 6,054,303 A | 4/2000 | Davalian et al. |
| 6,200,985 B1 | 3/2001 | Cottens et al. |
| RE37,421 E | 10/2001 | Holt et al. |
| 6,328,970 B1 * | 12/2001 | Molnar-Kimber et al. ........................ 424/184.1 |
| 6,455,518 B2 | 9/2002 | Zenke et al. |
| 6,541,612 B2 | 4/2003 | Molnar-Kimber et al. |

(Continued)

FOREIGN PATENT DOCUMENTS

EP     0 364 032     10/1989

(Continued)

OTHER PUBLICATIONS

Cattaneo et al., Therapeutic Drug Monitoring of Sirolimus: Effect of concomitent Immmunosuppressive Therapy and Optimization of Drug Doses, American Journal of Transplantation, Aug. 2004, vol. 4, pp. 1345-1351.* Maggio et al., Enzyme Immunoassay, CRC Press Inc., 1987, pp. 186-187.*
Yohannes, et al.,"Degradation of Rapamycin: Synthesis of . . . ", Tetrahedron Letters, (1993) vol. 34, No. 13, pp. 2075-2078.
Steffan, et al., "Base Catalyzed Degradations of Rapamycin", Tetrahedron Letters (1993), vol. 34, No. 23, pp. 3699-3702.
Luengo, et al., "Studies on the Chemistry of Rapamycin: Novel Transformations . . . ", Tetrahedron Letters (1993), vol. 34, No. 6, pp. 991-994.
D. Yohannes and S. Danishefsky, "Degradation of Rapamycin: Retrieval . . . ", Tetrahedron Letters, (1992), vol. 33, No. 49, pgs. 7469-7472.
Trepanier, et al., "Rapamycin: Distribution, Pharmacokinetics . . . ", Clinical Biochemistry, (1998) vol. 31, No, 5, pp. 345-351.
Jones, et al., "An Immunoassay for the Measurement of Sirolimus", Clinical Therapeutics (2000), vol. 22, supp. B, pp. B49-B61.
Davis et al."An Immunophilin-Binding Assay for Sirolimus", Clinical Therapeurtics (2000), vol. 22, supp. B, pp. B62-B70.
Salm, et al., "The Quantification of Sirolimus by High-Performance . . . ", Clinical Therapeutics (2000), vol. 22, supp. B, pp. B71-B85.

*Primary Examiner* — Melanie J Yu
*Assistant Examiner* — Gary Counts
(74) *Attorney, Agent, or Firm* — Theodore J. Leitereg; Robert N. Carpenter

(57) ABSTRACT

Methods and kits for determining sirolimus in a sample known or suspected to contain sirolimus are provided. The methods and kits according to the invention use one or more antibodies generated using a fragment of sirolimus, such as the northern fragment of sirolimus.

21 Claims, 4 Drawing Sheets

U.S. PATENT DOCUMENTS

| | | | |
|---|---|---|---|
| 6,635,745 B2 * | 10/2003 | Sedrani et al. | 530/405 |
| 6,677,357 B2 | 1/2004 | Zhu et al. | |
| 6,709,873 B1 * | 3/2004 | Yatscoff et al. | 436/547 |
| 2001/0010920 A1 | 8/2001 | Molnar-Kimber et al. | |

FOREIGN PATENT DOCUMENTS

| | | |
|---|---|---|
| EP | 0 401 747 B1 | 6/1990 |
| EP | 0 467 606 A1 | 7/1991 |
| EP | 0 509 795 A2 | 4/1992 |
| EP | 0 867 438 B1 | 9/1993 |
| EP | 0 593 227 A1 | 10/1993 |
| JP | 05-112573 A | 5/1993 |
| JP | 06-211870 A | 8/1994 |
| JP | 11-240884 A | 9/1999 |
| WO | WO 91/10907 | 7/1991 |
| WO | WO 92/19745 | 11/1992 |
| WO | WO 94/09010 | 4/1994 |
| WO | WO 94/24304 | 10/1994 |
| WO | WO 94/25022 | 11/1994 |
| WO | WO 94/25072 | 11/1994 |
| WO | WO 94/25468 | 11/1994 |

OTHER PUBLICATIONS

* cited by examiner

METHODS AND KITS FOR THE DETERMINATION OF SIROLIMUS IN A SAMPLE

FIELD OF THE INVENTION

The invention relates to methods and kits for the determination of sirolimus in samples known or suspected to contain sirolimus, such as patient samples.

BACKGROUND OF THE INVENTION

Sirolimus is a carbocyclic lactone-lactam macrolide produced by the bacterium streptomyces-hygroscopicus. In addition to its antibiotic and antifungal properties, sirolimus acts as a potent immunosuppressive agent. Indeed, sirolimus is frequently used to suppress immune function following transplant procedures. Sirolimus also has antiproliferative properties and has been used recently in conjunction with cardiac stents to prevent restenosis at treatment sites within body vessels.

Considering the widespread and growing use of sirolimus as a therapeutic agent in a variety of clinical procedures, the abilities to accurately detect sirolimus in a sample, such as a patient sample, and to determine concentrations of the compound have increasing importance. For example, it may be desirable to monitor concentrations of the compound in blood to ensure that an effective concentration has been reached and/or is being maintained. If necessary, adjustments to treatment dosages can be made based on the concentrations determined in an appropriate assay.

Current assays for the determination of sirolimus in whole blood samples include an assay based on high-performance liquid chromatography (HPLC) and mass spectrometry (MS) techniques. While HPLC and MS techniques may provide desired accuracy and sensitivity, these assays require specialized skill and equipment. Typically, these techniques are not conducted at clinical facilities and samples are often sent to independent laboratories for analysis, which introduces a delay into the testing program.

Immunoassay techniques, which use antibodies for the detection of an analyte in a sample, are relatively simple laboratory procedures and can often be conducted using automated equipment. Indeed, clinical laboratories typically have such equipment on-site, making immunoassays a desirable format for the analysis of patient samples.

Prior art immunoassays for the determination of sirolimus require the use of an antibody generated using the whole sirolimus compound. This may produce undesirable results because antibodies generated in this manner may cross-react with sirolimus metabolites that have little to no immunosuppressive or other therapeutic activity. For example, sirolimus is metabolized by cytochrome p450 3A enzymes to produce an array of metabolites, including demethylated metabolites that have negligible immunosuppressive activity. These metabolites can be present in patient samples at significant levels (as much as 10% for 16-0-demethyl and 39-0-demethyl species), making any cross-reactivity potentially significant.

Accordingly, there is a need for improved methods and kits for the determination of sirolimus in samples.

SUMMARY OF EXEMPLARY EMBODIMENTS OF THE INVENTION

The invention provides methods and kits for the determination of sirolimus in a test sample, such as a human whole blood sample. The methods and kits according to the invention use an antibody or antibodies generated using a fragment of the sirolimus compound. Exemplary embodiments of the invention use a monoclonal antibody generated using the northern fragment of the sirolimus compound coupled to a carrier.

In one exemplary embodiment, a method according to the invention comprises the steps of providing a sample known or suspected to contain sirolimus and providing an antibody preparation comprising one or more antibodies generated using a fragment of sirolimus. Another step of the method comprises contacting the antibody preparation with the sample. Another step comprises detecting binding between the one or more antibodies of the antibody preparation and sirolimus. In one particular embodiment, the antibody preparation comprises one or more antibodies generated using the northern fragment of sirolimus coupled to a carrier.

In another exemplary embodiment, a method according to the invention comprises the steps of providing a sample known or suspected of containing sirolimus, providing an antibody preparation comprising one or more antibodies generated using a fragment of sirolimus and bound to a first solid particle comprising a chemiluminescent dye, providing a second solid particle comprising a photosensitive dye and a first member of a specific binding pair, and providing a receptor capable of specifically binding sirolimus and bound to a second member of the specific binding pair that is able to bind to the first member of the specific binding pair. Another step of the method comprises contacting the sample with the antibody preparation, the second solid particle, and the receptor to form a reaction solution. Another step of the method comprises illuminating the reaction solution at a wavelength at which the photosensitive dye absorbs light. Another step of the method comprises measuring chemiluminescence produced by the chemiluminescent dye.

A kit according to one exemplary embodiment of the invention comprises an antibody preparation comprising one or more antibodies generated using a fragment of sirolimus and bound to a solid particle containing a chemiluminescent dye, one or more second solid particles comprising a photosensitive dye and a first member of a specific binding pair, and a receptor that specifically binds sirolimus and is bound to a second member of the specific binding pair that is able to bind to the first member of the specific binding pair.

Additional understanding of the invention can be obtained with review of the detailed description of exemplary embodiments of the invention, appearing below, and the appended drawings.

DETAILED DESCRIPTION OF EXEMPLARY EMBODIMENTS OF THE INVENTION

The following provides a detailed description of various exemplary embodiments of the invention. The embodiments described herein are exemplary in nature, and serve simply as examples to aid in enabling one of ordinary skill in the art to make and use the invention. The description of exemplary embodiments is not intended to limit the scope of the invention, or its protection, in any manner.

Figure 1:
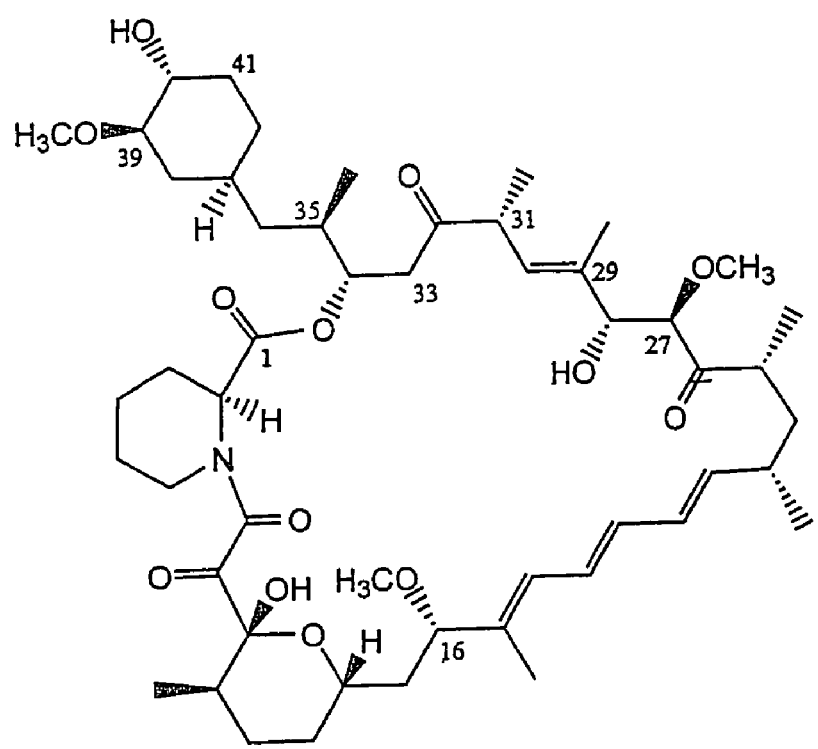
FIG. 1 is a schematic of the sirolimus compound.

The sirolimus compound is a stable cyclic compound that has immunosuppressive and antiproliferative properties, among others. FIG. 1 is a schematic of the whole, unmetabolized sirolimus compound. It is noted that two different ring-numbering systems have been used in the art for sirolimus. All references to numbered positions on the sirolimus compound presented herein are made with reference to the numbering presented in FIG. 1.

The methods and kits of the invention use one or more antibodies generated using a fragment of the sirolimus compound. As used herein, the term "generated using" refers to an antibody or antibodies produced as part of an immune response to a particular composition. The antibody or antibodies can be produced during the actual immune response, or by cells derived from or otherwise biologically related to cells that participated in the immune response to the composition.

Figure 2:
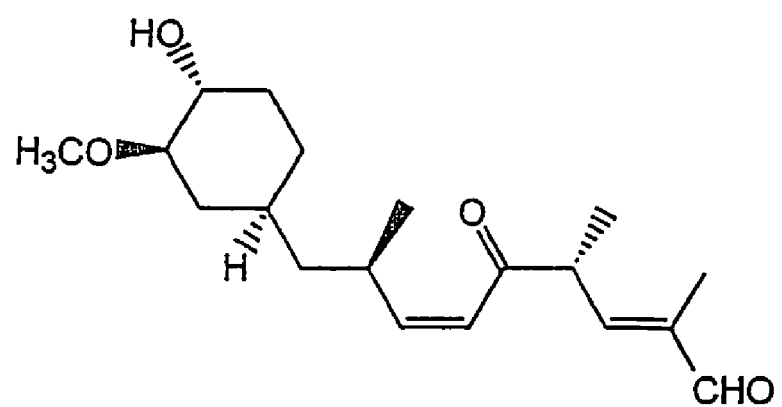
FIG. 2 is a schematic of the northern fragment of the sirolimus compound.
Figure 3:
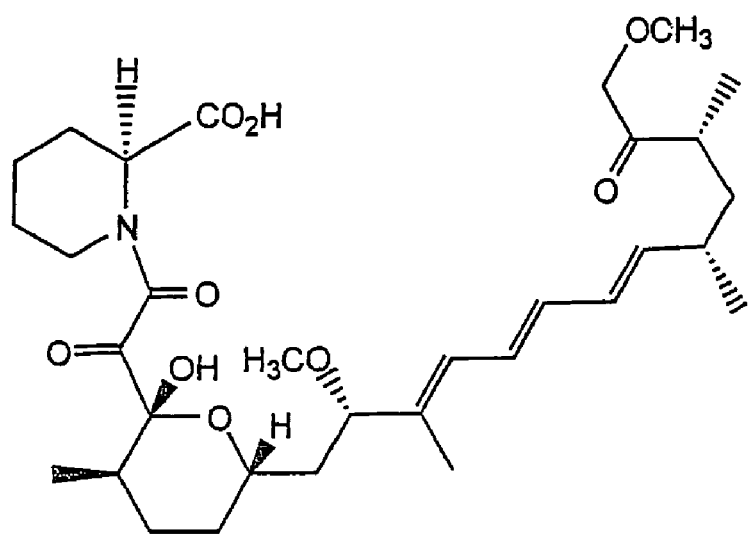
FIG. 3 is a schematic of the southern fragment of the sirolimus compound.

In the generation of antibodies, any suitable fragment of the sirolimus compound can be used. In exemplary embodiments, one or more antibodies generated using the northern fragment of the sirolimus compound are used. The northern fragment includes C28 through C42 and is illustrated in FIG. 2. FIG. 3 is a schematic of the southern fragment of the sirolimus compound, which can also be used in the generation of antibodies for use in the methods and kits of the invention. Further, a derivative of a fragment of the sirolimus compound can be used. As used herein, the term "derivative" refers to a chemical composition that represents a modified form of another chemical composition. Modifications can include addition of one or more elements and chemical groups, removal of one or more elements or chemical groups, and substitution of one or more elements or chemical groups for others. The derivative need only be sufficient to generate the desired antibody or antibodies as described herein.

Antibodies generated using the northern fragment are considered advantageous at least because the fragment includes an unmetabolized methoxy group at C39. Sirolimus containing demethylated C39 is a significant sirolimus metabolite that has negligible immunosuppressive activity. Antibodies generated using the entire sirolimus compound may not be able to discriminate between the entire sirolimus compound and the demethylated C39 metabolite. As a result, these antibodies may give inaccurate results in sirolimus assays, such as concentration determinations. In contrast, it is believed that antibodies generated using the northern fragment, with its unmetabolized C39, will have an epitope specificity towards sirolimus species with the unmetabolized C39 methoxy group. Antibodies with this epitope specificity are expected to show substantially no specific binding to sirolimus metabolites containing a demethylated C39, minimizing any potentially misleading results due to cross-reactivity.

Figure 4:
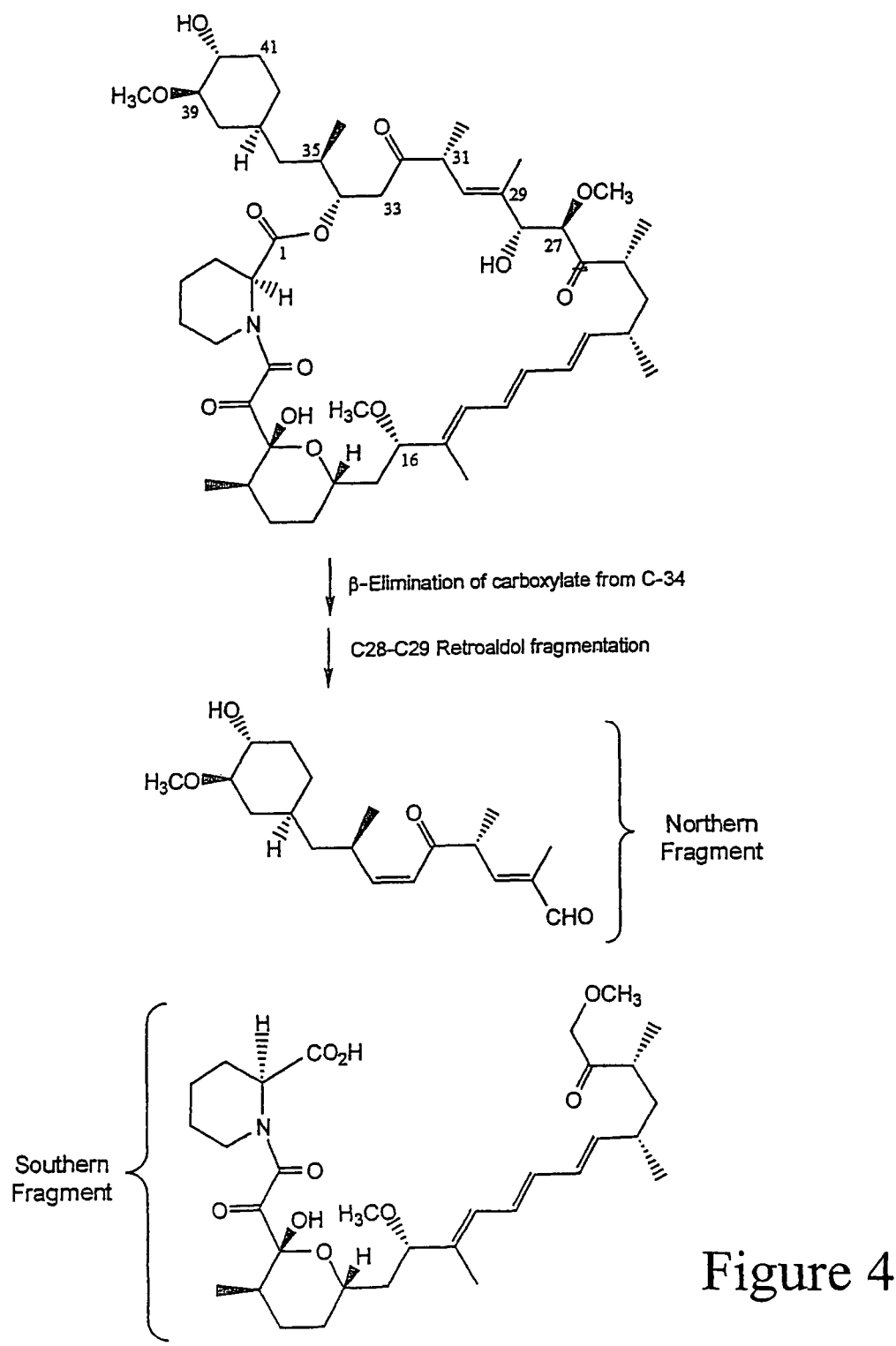
FIG. 4 is a schematic of a chemical process for generating the northern fragment from the whole sirolimus compound.

The northern fragment of sirolimus can be prepared using two sequential ring cleavage reactions. This preparation scheme is illustrated in FIG. 4. First, a base-catalyzed β-elimination of the pipecoline-carboxylate moiety from C34 is conducted. This step can be performed using NaOH (see Yohannes, et al., Tetrahedron Lett. 1993, 34:2075-2078) or diethylamine in methanol, DMAP in refluxing $CH_2Cl_2$ (Id) or DBU in THF (Id, see also Luengo et al., Tetrahedron Lett. 1993, 34: 991-994). Second, a retroaldol fragmatation of the C27-C28 bond is conducted by treatment of the product of the first step. This step can be performed by treating the product of the first step with a base; such as methanolic NaOH or LDA/THF, or with a Lewis acid, such as $ZnCl_2$/THF (Luengo et al., Tetrahedron Lett. 1993, 34: 991-994). Following the second step, two fragments are produced: the C28-C42 northern fragment and the C1-C27 southern fragment.

The resulting northern fragment contains the intact hydroxy-methoxy-cyclohexane ring attached to a carbon chain that terminates in an aldehyde. The structure of the northern fragment is amenable to linkage of the fragment to a carrier. For example, the northern fragment can be linked to surface lysine residues in a protein carrier by reductive alkylation with sodium cyanoborohydride. Linkage of the northern fragment to a protein carrier can facilitate preparation of antibodies directed against the fragment by conferring immunogenicity onto the compound. Any suitable carrier can be used, and the specific carrier chosen need only be amenable to linkage to the northern fragment and be sufficiently immunogenic to produce an appropriate antibody response in a biological system used to generate antibodies, such as mice and rabbits. Specific, non-limiting examples of suitable carriers include ovalbumin, keyhole limpet hemocyanin (KLH) and hen eggwhite lysozyme (HEL).

As described above, any suitable fragment of the sirolimus compound can be used in the generation of antibodies for use in the invention. The fragment is advantageously selected so that antibodies generated using the fragment show minimal levels of specific binding to one or more sirolimus metabolites. The southern fragment of the sirolimus compound is another currently contemplated fragment for use in generation of antibodies for use in the invention.

Antibodies for use in the methods and kits of the invention can be generated using any suitable technique, including conventional techniques for the preparation of monoclonal antibodies. In one specific example, the northern fragment, bound to ovalbumin as carrier, is injected into mice and hybridomas are prepared. Clonal selection techniques are used to detect and raise hybridomas that produce antibodies with specific binding for the whole sirolimus compound. The antibodies that show a desired level of binding to whole sirolimus can also be screened for no or minimal levels of binding to one or more sirolimus metabolites, such as demethylated C39 metabolites. In specific examples, one or more hybridomas producing antibodies that specifically bind to the whole sirolimus compound but that show no or minimal levels of specific binding to one or more sirolimus metabolites are detected and selected. These hybridomas are expanded and a cell line is established.

It is understood that other antibody-producing techniques can be used. For example, polyclonal antibody preparations can be used in the methods and kits according to the invention and any suitable technique for generating polyclonal antibodies directed against a fragment of the sirolimus compound can be used. Accordingly, a suitable animal, such as a rabbit, can be immunized with a northern fragment-carrier conjugate, and serum preparations can be harvested at one or more appropriate time intervals. Also, an ascites fluid containing polyclonal antibodies specific for sirolimus can be prepared and harvested using a northern fragment-carrier conjugate and conventional techniques.

The invention provides methods for determining sirolimus in a sample. The methods of the invention can be used to determine sirolimus in any sample known or suspected to contain sirolimus. Accordingly, the sample can be a sample from a solution prepared in a laboratory or other setting, and also can be a sample taken from a patient, such as a human or other animal. Patient samples can be taken from any suitable source, including various body fluids. For sirolimus dose monitoring and other methods having clinical significance, whole blood samples are advantageously used because the vast majority of sirolimus in vivo is associated with red blood cells in patients receiving sirolimus treatment.

The methods for determining sirolimus in a sample use an antibody preparation that includes one or more antibodies that has been generated using a fragment of the sirolimus compound. In exemplary embodiments, the antibody preparation is a monoclonal antibody preparation generated using the northern fragment of the sirolimus compound bound to a carrier.

One exemplary method according to the invention includes the step of providing an antibody preparation that includes one or more antibodies generated using a fragment of the sirolimus compound. The antibody preparation can be any suitable antibody preparation, including a monoclonal antibody preparation, a polyclonal antibody preparation, and other suitable antibody preparations. Another step of the method comprises contacting the antibody preparation with a sample known or suspected of containing sirolimus. Another step of the method comprises detecting binding of one or more antibodies of the antibody preparation to sirolimus.

The step of contacting the antibody preparation can be conducted in any suitable reaction vessel, and the specific reaction vessel chosen will depend on several considerations, including the volume and nature of the sample. Microtiter plates are considered advantageous at least because of their structure and convenient format, which facilitates efficient analysis of multiple samples.

The step of detecting binding of one or more antibodies of the antibody preparation to sirolimus can be conducted using any suitable techniques and the specific technique chosen will depend on several considerations, including the type of equipment available for conducting this step. Non-limiting examples of suitable techniques for detecting binding include detection of optical properties of a solution that are dependent on the presence of sirolimus in the solution. For example, one or more antibodies in an antibody preparation can be labeled with an enzyme that converts a substrate to produce a color change. The substrate is added to a reaction vessel after the contacting step and any desired washing steps. Any resultant color change in the substrate is due to labeled antibody that has bound to sirolimus.

A variety of optional steps can be included in methods according to the invention. For example, a step of determining the concentration of sirolimus in the sample can be included. The concentration can be determined using any suitable technique, including by comparison of binding data, obtained from conducting a method according to the invention, to a standard curve that correlates binding data to a series of known concentrations of sirolimus. The standard curve can be prepared using the antibody preparation and a series of solutions having known concentrations of sirolimus.

The methods of the invention can be used in a variety of assays for determining sirolimus in a sample. Indeed, the methods of the invention can be used in any immunoassay in which one or more antibodies are used to bind to sirolimus to detect sirolimus in a sample. Exemplary types of assays in which the methods of the invention can be used include radio immunoassays (RIA), enzyme-linked immunosorbent assays (ELISA), and microparticle enzyme immunoassays (MEIA).

An exemplary assay according to the invention is a Luminescent Oxygen Channeling Immunoassay (LOCI). This assay measures chemiluminescence generated by a photochemically activatable chemiluminescent compound (PACC) in response to singlet oxygen or another activator. The chemiluminescence generated in a LOCI is directly proportional to the amount of the analyte of interest in a sample because the activator is released from a photosensitive dye that is associated with the analyte through specific binding. LOCI analyses can be conducted in sandwich and competitive immunoassay formats and advantageously include appropriate binding reagents associated with solid particles, such as beads, including latex microbeads.

Example 1 describes a suitable LOCI for determining sirolimus in a sample according to the invention.

The invention also provides kits useful for determining sirolimus in a sample known or suspected to contain sirolimus. The kits according to the invention are useful in the determination of sirolimus in a variety of samples, including human and other animal samples. Kits according to the invention include at least one antibody generated using a fraction of the whole sirolimus compound. In exemplary embodiments, kits according to the invention include a monoclonal antibody generated using the northern fragment of the sirolimus compound bound to a carrier. In one particular example, a kit according to the invention includes a monoclonal antibody generated using the northern fragment of the sirolimus compound bound to KLH.

The kits according to the invention can include additional optional components, such as one or more solutions containing a predetermined concentration of the whole sirolimus compound. These solutions can be used as reference controls in an assay for determining sirolimus in a sample. A solution containing a sirolimus metabolite, such as a demethylated metabolite of sirolimus, can also be included. In one particular example, a solution containing sirolimus demethylated at C39 is included. This solution can be used as a reference control in assays for determining sirolimus that use antibodies generated using the unmetabolized northern fragment, and are expected to control for any background binding with sirolimus demethylated at C39.

Kits according to the invention can also include optional components that facilitate detection of binding between the included at least one antibody and sirolimus within a sample being evaluated. The specific optional components included in any particular kit will depend on the type of assay in which the kit will be used. In one particular example, a kit includes components for use in a LOCI. In this example, the kit includes one or more PACCs, one or more photosensitive dyes, and one or more beads. This kit can also include various control solutions, such as those described above.

Example 2 describes a suitable kit useful in a LOCI for determining sirolimus according to the invention.

A kit according to one exemplary embodiment of the invention comprises two bead reagents and a biotinylated sirolimus binding compound. The biotinylated sirolimus binding compound can be any suitable compound that is able to specifically bind sirolimus, such as a monoclonal antibody preparation, a polyclonal antibody preparation, and a non-antibody sirolimus binding protein, such as FK506 binding protein (FKBP). FKBP is a binding protein associated with red blood cells that is able to specifically bind sirolimus.

In this exemplary embodiment, the components of the kit are particularly well-suited for use in LOCI techniques. Accordingly, the first bead reagent is coated with streptavidin and contains a photosensitive dye. The second bead reagent contains a chemiluminescent dye and is coated with one or more antibodies generated using a fragment of the sirolimus compound and capable of binding to unmetabolized sirolimus. The one or more antibodies are advantageously monoclonal antibodies generated using the northern fragment of the sirolimus compound. Alternatively, a polyclonal antibody preparation can be used as the one or more antibodies. If used, the polyclonal antibody preparation can be generated using any suitable fragment of the sirolimus compound, including the northern fragment.

Example 1

LOCI Suitable for Determining Sirolimus in a Sample

Sirolimus can be determined in a sample according to the invention using LOCI techniques. This example generally describes a LOCI technique suitable for such evaluations.

Two latex bead reagents and a biotinylated analyte receptor are used. One bead reagent, termed sensibead, is coated with streptavidin and contains a photosensitive dye. A second bead reagent, termed chemibead, is coated with one or more antibodies generated using a fragment of the sirolimus compound and capable of binding the whole, unmetabolized sirolimus compound. The chemibead contains a chemiluminescent dye. In this assay, biotinylated FKBP can be used as the biotinylated analyte receptor.

To conduct the assay, the three reagents are combined in a reaction vessel with the sample of interest. If sirolimus is present in the sample, a bead-aggregated immunocomplex is formed. The sirolimus binds to the FKBP and the antibody on the chemibead, and the streptavidin on the sensibead binds to the biotin on the FKBP to create the immunocomplex. The sample is subsequently illuminated at a wavelength at which the photosensitive dye is able to absorb light. Singlet oxygen is generated by the sensibeads due to the absorption of light. Due to the proximity of the sensibeads and chemibeads in the immunocomplex, which only forms if sirolimus is present in the sample, the singlet oxygen diffuses into the chemibeads and triggers a chemiluminescent reaction with the chemiluminescent dye. Finally, the resultant chemiluminescence is measured and correlated with a standard curve to determine the concentration of sirolimus present in the sample.

Sensibeads containing a photosensitive dye that is able to absorb light at 680 nm are suitable for use in this assay. Also, chemibeads containing a chemiluminscent dye that generates chemiluminescence detectable at 612 nm are suitable for use in this assay.

Example 2

Kit Useful in a LOCI for Determining Sirolimus in a Sample

One kit according to an exemplary embodiment of the invention includes the following components:
1. An antibody generated using the northern fragment of the sirolimus compound. The antibody is bound to one or more beads that contain a chemiluminescent dye ("chemibeads").
2. One or more beads containing a photosensitive dye ("sensibeads").
   Each of the one or more sensibeads is coated with streptavidin.
3. A preparation of biotinylated FKBP.
   Optional components in this kit include control solutions as described above.

The foregoing detailed description provides exemplary embodiments of the invention and includes the best mode for practicing the invention. These embodiments are intended only to serve as examples of the invention, and not to limit the scope of the invention, or its protection, in any manner.

I claim:
1. A method for determining sirolimus in a sample, comprising:
   providing a sample known or suspected to contain sirolimus;
   providing an antibody preparation comprising one or more antibodies generated using a compound consisting of the formula:

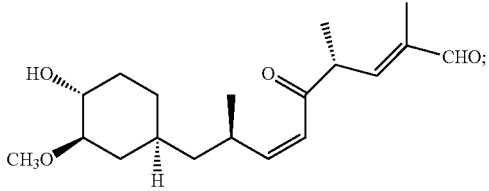

contacting the antibody preparation with the sample; and
   detecting binding between the one or more antibodies and sirolimus.
2. The method for determining sirolimus in a sample according to claim 1, wherein the sample comprises a human sample.
3. The method for determining sirolimus in a sample according to claim 1, wherein the sample comprises a whole blood sample.
4. The method for determining sirolimus in a sample according to claim 1, wherein the antibody preparation comprises a monoclonal antibody.
5. The method for determining sirolimus in a sample according to claim 4, wherein the monoclonal antibody specifically binds whole sirolimus and does not specifically bind metabolized sirolimus.
6. The method for determining sirolimus in a sample according to claim 4, wherein the monoclonal antibody is bound to a solid particle.
7. The method for determining sirolimus in a sample according to claim 1, wherein the one or more antibodies specifically bind whole sirolimus and do not specifically bind metabolized sirolimus.
8. The method for determining sirolimus in a sample according to claim 1, wherein the antibody preparation comprises one or more antibodies generated using a compound consisting of the formula:

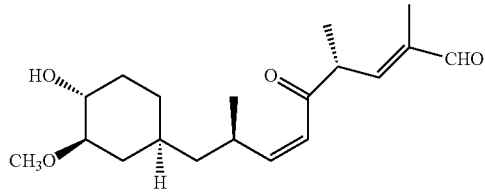

bound to a carrier.
9. The method for determining sirolimus in a sample according to claim 8, wherein the carrier comprises a protein.
10. The method for determining sirolimus in a sample according to claim 9, wherein the carrier comprises one of ovalbumin, keyhole limpet hemocyanin, and hen eggwhite lysozyme.
11. The method for determining sirolimus in a sample according to claim 1, further comprising the step of determining the concentration of sirolimus in the sample based upon the step of detecting binding between the one or more antibodies and sirolimus.

12. A method for determining a concentration of sirolimus in a sample, the method comprising:
contacting a sample known or suspected to contain sirolimus with an antibody preparation comprising one or more antibodies generated using a compound consisting of the formula:

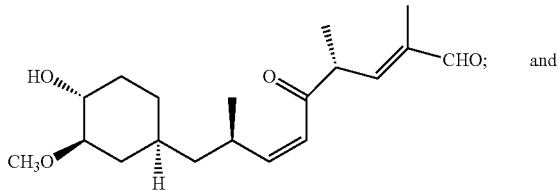

determining the concentration of sirolimus in the sample by correlating the binding between the one or more antibodies and sirolimus in the sample to a series of known concentrations of sirolimus.

13. The method for determining a concentration of sirolimus in a sample according to claim 12, wherein the sample comprises a human sample.

14. The method for determining a concentration of sirolimus in a sample according to claim 12, wherein the sample comprises a whole blood sample.

15. The method for determining a concentration of sirolimus in a sample according to claim 12, wherein the antibody preparation comprises a monoclonal antibody.

16. The method for determining a concentration of sirolimus in a sample according to claim 15, wherein the monoclonal antibody specifically binds whole sirolimus and does not specifically bind metabolized sirolimus.

17. The method for determining a concentration of sirolimus in a sample according to claim 15, wherein the monoclonal antibody is bound to a solid particle.

18. The method for determining a concentration of sirolimus in a sample according to claim 12, wherein the one or more antibodies specifically bind whole sirolimus and do not specifically bind metabolized sirolimus.

19. The method for determining a concentration of sirolimus in a sample according to claim 12, wherein the antibody preparation comprises one or more antibodies generated using the compound bound to a carrier.

20. The method for determining a concentration of sirolimus in a sample according to claim 19, wherein the carrier comprises a protein.

21. The method for determining a concentration of sirolimus in a sample according to claim 20, wherein the carrier comprises one of ovalbumin, keyhole limpet hemocyanin, and hen eggwhite lysozyme.

* * * * *